US009259353B2

(12) United States Patent
Dos Santos et al.

(10) Patent No.: US 9,259,353 B2
(45) Date of Patent: Feb. 16, 2016

(54) CAPILLARY ACTION IN FLOW-REGULATING SYSTEMS

(71) Applicant: Alcon Research, Ltd., Fort Worth, TX (US)

(72) Inventors: Cesario P. Dos Santos, Alisa Viejo, CA (US); Nicholas M. Gunn, Newport Beach, CA (US); Leslie A. Field, Portola Valley, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 610 days.

(21) Appl. No.: 13/649,354

(22) Filed: Oct. 11, 2012

(65) Prior Publication Data

US 2014/0107557 A1   Apr. 17, 2014

(51) Int. Cl.
*A61M 5/00*    (2006.01)
*A61F 9/007*   (2006.01)

(52) U.S. Cl.
CPC ................................. *A61F 9/00781* (2013.01)

(58) Field of Classification Search
CPC ... A61F 9/00781; A61F 9/007; A61B 5/0084; A61M 27/002; A61M 2210/0612
USPC .......... 604/8–10, 133; 606/106–107; 623/4.1, 623/1.12; 424/422, 423
See application file for complete search history.

(56) References Cited

U.S. PATENT DOCUMENTS

| 8,956,320 | B2* | 2/2015 | Ovchinnikov et al. ........... 604/9 |
| 2009/0306594 | A1* | 12/2009 | Pang et al. .................... 604/133 |
| 2010/0120018 | A1* | 5/2010 | Quake et al. ....................... 435/5 |
| 2011/0071458 | A1* | 3/2011 | Rickard ........................... 604/9 |

OTHER PUBLICATIONS

International Preliminary Report on Patentability issued for PCT/US2013/064053 dated Apr. 23, 2015, 7 pages.
PCT/US2013/064053, International Search Report and Written Opinion, International Searching Authority, Dec. 16, 2013, 8 pgs.

* cited by examiner

*Primary Examiner* — Philip R Wiest
(74) *Attorney, Agent, or Firm* — Haynes and Boone, LLP

(57) ABSTRACT

A fluid flow-regulating system includes an electrolysis chamber configured to contain a liquid, and includes first and second electrodes disposed within the electrolysis chamber. A gap between opposing surfaces is sized to promote capillary action of a liquid in the electrolysis chamber that draws the liquid to at least one of the first and second electrodes in a manner allowing the flow-regulating system to be placed in multiple orientations and still have said one of the first and second electrodes wetted by capillary action.

17 Claims, 5 Drawing Sheets though the trabecular meshwork and the uveoscleral pathways, both of which contribute to the aqueous humor drainage system. The delicate balance between the production and drainage of aqueous humor determines the eye's IOP.
CAPILLARY ACTION IN FLOW-REGULATING SYSTEMS

BACKGROUND

The present disclosure relates generally to flow-regulating system devices and associated systems and methods for use in ophthalmic treatments.

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous humor drainage system. The delicate balance between the production and drainage of aqueous humor determines the eye's IOP.

FIG. 1 is a diagram of the front portion of an eye that helps to explain the processes of glaucoma. In FIG. 1, representations of the lens 10, cornea 20, iris 30, ciliary body 40, trabecular meshwork 50, Schlemm's canal 60, and anterior chamber 70 are pictured. Anatomically, the anterior segment of the eye includes the structures that cause elevated IOP which may lead to glaucoma. Aqueous humor fluid is produced by the ciliary body 40 which lies beneath the iris 30 and adjacent to the lens 10 in the anterior segment of the eye. This aqueous humor washes over the lens 10 and iris 30 and flows to the drainage system located in the angle of the anterior chamber 70. The angle of the anterior chamber 70, which extends circumferentially around the eye, contains structures that allow the aqueous humor to drain. The trabecular meshwork 50 is commonly implicated in glaucoma. The trabecular meshwork 50 extends circumferentially around the anterior chamber 70. The trabecular meshwork 50 seems to act as a filter, limiting the outflow of aqueous humor and providing a back pressure that directly relates to IOP. Schlemm's canal 60 is located beyond the trabecular meshwork 50. Schlemm's canal 60 is fluidically coupled to collector channels (not shown) allowing aqueous humor to flow out of the anterior chamber 70. The two arrows in the anterior segment of FIG. 1 show the flow of aqueous humor from the ciliary bodies 40, over the lens 10, over the iris 30, through the trabecular meshwork 50, and into Schlemm's canal 60 and its collector channels.

One method of treating glaucoma includes implanting a drainage device in a patient's eye. The drainage device allows fluid to flow from the anterior chamber of the eye to a drainage site, relieving pressure in the eye and thus lowering IOP. In order to provide desired treatments to patients, it may be important to regulate the drainage flow through the drainage device.

The system and methods disclosed herein overcome one or more of the deficiencies of the prior art.

SUMMARY

In an exemplary aspect, the present disclosure is directed to a fluid flow-regulating system, including an electrolysis chamber configured to contain a liquid, and including first and second electrodes disposed within the electrolysis chamber. A gap between opposing surfaces is sized to promote capillary action of a liquid in the electrolysis chamber that draws the liquid to at least one of the first and second electrodes in a manner allowing the flow-regulating system to be placed in multiple orientations and still have said one of the first and second electrodes wetted by capillary action.

In an aspect, one of the opposing surfaces is a surface of one of the first and second electrodes and another of the opposing surfaces is a flexible membrane. In another aspect, the first and second electrodes extend adjacent an apex of the flexible membrane.

In yet another aspect, the opposing surfaces are surfaces of a capillary channel having an opening adjacent one of the first and second electrodes. In another aspect, a sub-chamber is within the electrolysis chamber, and the first and second electrodes are disposed within the sub-chamber and the opening of the passageway opens into the sub-chamber.

In another exemplary aspect, the present disclosure is directed to a fluid flow-regulating system for an ocular implant sized for implantation in an eye of a patient for treating an ocular condition. The system may include a housing including an entrance port and an exit port connected by a fluid flow passageway. A gas generation chamber may be disposed within the housing. A gas generating element may be associated with the gas generation chamber, and may be operable to convert liquid to gas. A gap between opposing surfaces may be sized to promote capillary action of a liquid in the gas generation chamber that draws the liquid to the gas generating element in a manner allowing the housing to be placed in multiple orientations and still have the gas generating element wetted by capillary action. A displaceable member may be disposed between the fluid flow passageway and the gas generation chamber. The displaceable member may be moveable relative to the fluid flow passageway to affect fluid flow through the passageway.

In one aspect, the gas generating element comprises an anode electrode and a cathode electrode and is operable to convert liquid to gas via an electrolysis process. In an aspect, one of said opposing surfaces is a surface of the gas generating element and another of said opposing surfaces is the displaceable member. In an aspect, said opposing surfaces are surfaces of a capillary channel having an opening adjacent the gas generating element.

In another exemplary aspect, the present disclosure is directed to a method including converting liquid to gas via an electrolysis process using electrodes in a gas generation chamber and changing the volume of the gas generation chamber, feeding additional liquid to the electrodes via capillary action, and converting the additional liquid to gas via the electrolysis process to further change the volume of the gas generation chamber.

In yet another exemplary aspect, the method may include draining liquid from an eye of a patient to treat an ocular condition, and regulating flow of the liquid by changing the volume of the gas generation chamber. In an aspect, regulating the flow of the liquid may comprise receiving data indicative of pressure from sensors, wherein converting liquid to gas occurs as a result of the received data; and expanding a flexible membrane into a fluid flow passageway carrying the draining liquid to increase or decrease the flow of fluid through the fluid flow passageway, wherein expanding the flexible membrane occurs as a result of changing the volume of the gas generation chamber.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
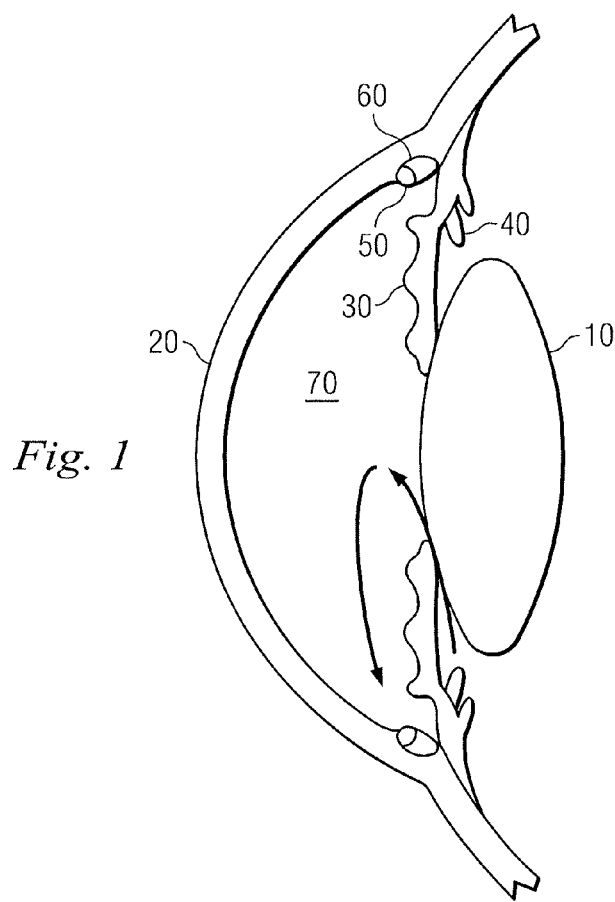
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to electrolysis-based flow-regulating systems for draining fluid from an anterior chamber of an eye, and in particular to devices that operate regardless of physical orientation of the device. In the exemplary embodiments disclosed, electrolysis-based flow-regulating systems utilize deflection of a membrane in response to pressure differentials across the membrane to regulate the flow through the device. These pressure differentials may be obtained using phase-change processes that convert liquid to gas. However, if the device is oriented so that the electrodes lie in the gaseous region, additional liquid-to-gas conversion does not as readily occur.

Such electrolysis-based flow-regulating systems include, by way of non-limiting example, valves and pumps. In some instances, embodiments of the present disclosure are configured to be part of an IOP control system. Those skilled in the art will realize that the flow control chambers disclosed herein may be utilized in similar applications where orientation can vary or there is a change that liquid to gas converters may become out of contact with the liquid.

The electrolysis-based flow-regulating systems disclosed herein are configured to have gas generating elements, such as electrodes, wetted even with the gas generating chamber placed in multiple orientations. Accordingly, if the flow-regulating system is placed in an eye, the electrodes may remain wetted whether the patient is standing, lying down, or otherwise oriented. Thus, the flow-regulating systems disclosed herein may optimize the performance of electrolysis-based devices utilizing flow-regulating systems within an IOP control system.

Figure 2:
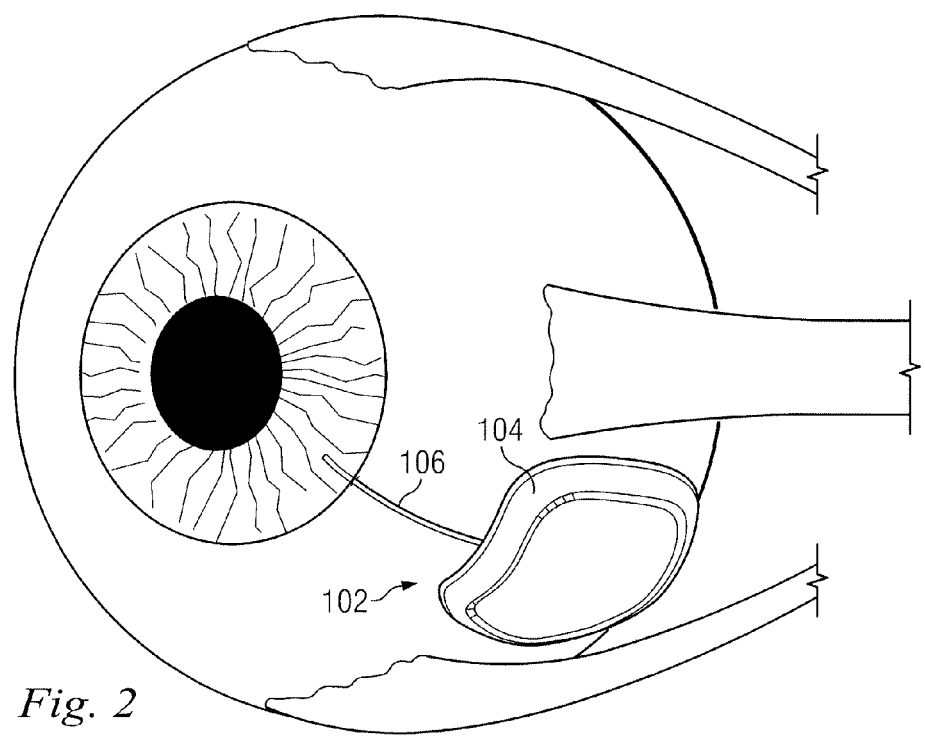
FIG. 2 is an illustration of an exemplary flow-regulating system disposed in the eye in accordance with one embodiment of the present disclosure.

FIG. 2 shows an exemplary implantable flow-regulating actuator 102 as an exemplary flow-regulating system disposed on an eye to treat an ocular condition according to one exemplary aspect of the present disclosure. The flow-regulating actuator 102 includes a body referred to herein as a plate 104 and a drainage tube 106 that extends from the plate 104. The plate 104 is arranged to carry various components of an IOP control system, and may include a valve, pump, transducers or sensors, a processing system and memory, drug delivery components, a power source or other components that may be used to either control the flow-regulating actuator 102 or otherwise treat ocular conditions.

The plate 104 is configured to fit at least partially within the subconjunctival space and is sized for example within a range between about 15 mm×12 mm to about 30 mm×15 mm and has a thickness less than about 2 mm thick and preferably less than about 1 mm thick. The plate 104 may be formed to the radius of the eye globe (about 0.5 inches). It may be rigid and preformed with a curvature suitable to substantially conform to the globe or it may be flexible to conform to the globe. Some embodiments are small enough that conforming to the globe provides little benefit in comfort or implantation technique. The above dimensions are exemplary only, and other sizes and arrangements are contemplated. When implanted, the plate 104 may be located in the subconjunctival pocket between the conjunctiva and sclera. It may be generally located on an ocular quadrant commonly used for conventional glaucoma drainage devices with plates; that is, it may be centered such that it is equidistant from the neighboring ocular muscles that define the ocular quadrant chosen for implantation.

The drainage tube 106 is sized to bridge the anterior chamber and the plate 104 in the subconjunctival pocket to provide an auxiliary flow path for aqueous humor, bypassing the flow-resistive conventional pathway through the trabecular meshwork and shunting aqueous humor directly to a drainage site. In the example shown, the drainage tube 106 is a single tube having a single lumen. Other embodiments include a plurality of drainage tubes or a plurality of lumens cooperating together to permit fluid to flow through the flow-regulating actuator 102. The drainage tube 106 is sized to extend from the plate 104 to the anterior chamber of the eye, as shown in FIG. 2. Aqueous humor may drain through the drainage tube from the anterior chamber to and out of the plate 104 to alleviate elevated intraocular pressure conditions.

Figure 3:
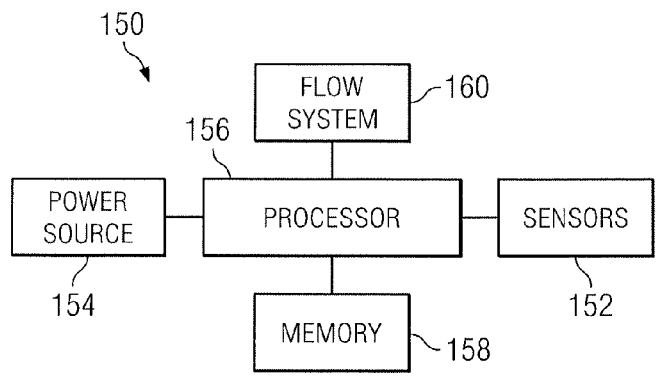
FIG. 3 is a block diagram of an exemplary IOP control system according to the principles of the present disclosure.

FIG. 3 is a block diagram of an exemplary IOP control system 150 forming a part of the flow-regulating actuator 102. The IOP control system 150 is configured in a manner that provides IOP pressure control, reducing complications arising from surgical implant glaucoma treatments. In FIG. 3, the IOP control system 150 includes one or more sensors 152, a power source 154, a processor 156, a memory 158, and a flow system 160.

The one or more sensors 152 may be configured to detect a parameter relating to the condition of the patient or the condition of the flow-regulating actuator 102. In one embodiment, the one or more sensors 152 are pressure sensors disposed about the flow-regulating actuator 102 and configured to detect pressure or variations in pressure. For example, the sensors may be used to detect pressures for calculation of IOP. Data from the sensors may be communicated to the processor 156 for processing.

The power source 154, which provides power to the system 150, is typically a rechargeable battery, such as a lithium ion or lithium polymer battery, although other types of power sources may be employed. The power source can be recharged via inductive coupling such as an RFID link or other type of magnetic coupling.

The processor 156 is typically an integrated circuit with power, input, and output pins capable of performing logic functions. In various embodiments, the processor 156 may be a targeted device controller or a microprocessor configured to control more than one component of the device. It may receive and process data and may issue control signals to the flow system or other components.

The memory 158, which is typically a semiconductor memory such as RAM, FRAM, or flash memory, interfaces with the processor 156. As such, the processor 156 can write to and read from the memory 158, and perform other common functions associated with managing semiconductor memory. In this manner, a series of IOP readings can be stored in the memory 158.

The flow system 160 controls the regulation of the amount of drainage flow through the flow-regulating actuator 102. In one embodiment, it is responsive to signals from the processor 156 to increase flow, decrease flow, or maintain flow.

The flow system 160 may be controlled by the processor 156 based on input data received from, by way of non-limiting example, sensors or data or a programmed treatment plan. A desired pressure differential (that corresponds to a flow rate) can be maintained by controlling the operation of the flow system 160. Likewise, various intraocular pressure parameters, such as, by way of non-limiting example, the desired IOP, the IOP change rate, and/or the bleb pressure may be controlled by controlling the operation of flow system 160.

Figure 4:
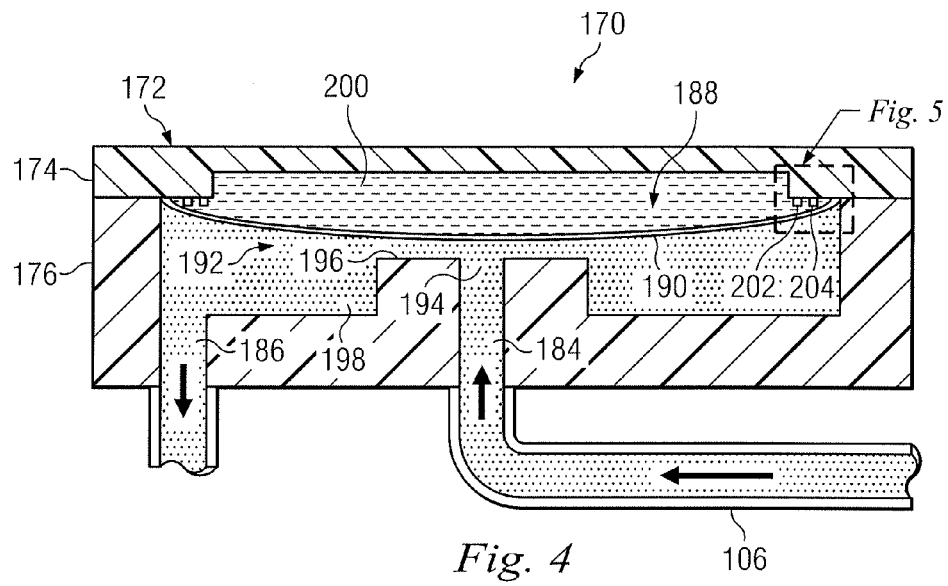
FIG. 4 is stylized illustration of a cross-sectional view of an exemplary flow system that may be a part of an exemplary IOP control system according to the principles of the present disclosure.

FIG. 4 shows a stylized cross-sectional view of an exemplary flow system 170 carried by or forming a part of the plate 104. The flow system 170 may correspond to the flow system 160 in FIG. 3. It includes a housing 172 having a chamber portion 174 and a flow portion 176, where the flow portion 176 includes an entrance port 184 and an exit port 186. The flow system 170 also includes a flow control system 188, and a fluid flow passageway 192 extending between the entrance port 184 and the exit port 186. The entrance port 184 connects to the drainage tube 106 (FIG. 2) and is configured to receive aqueous flowing from the drainage tube 106. The exit port 186 permits fluid to exit the housing 172 for release at a drainage site or for further regulation.

The flow control system 188 includes a flexible membrane 190 defining at least in part a gas generation chamber 200, and a plurality of electrodes 202, 204. The flexible membrane 190 may be formed of an elastically deformable elastomeric including without limitation, materials such as a silicone, silicon nitride, silicone elastomeric, polyimide, parylene and others. In the example shown, the flexible membrane is secured to the housing 172 at its edges. In one embodiment, the flexible membrane 190 is a circular material secured at its periphery to the housing 172. In other embodiments, the housing 172 and flexible membrane 190 are formed so that the membrane has a circular, non-circular shape, including oval, substantially rectangular, or square, for example. Other shapes are also contemplated.

The gas generation chamber 200 is fluid filled with an actuator liquid and includes the electrodes 202, 204 disposed within the actuator liquid in a manner permitting at least a portion of the ions and electrolytes in the actuator liquid to phase change from liquid to gas, forming gas-filled bubbles within the gas generation chamber 200 through electrolysis. As the gas bubbles form, the pressure in the gas generation chamber 200 increases, displacing the membrane 190 into the fluid flow passageway 192. The electrodes 202, 204 are in electrical communication with the power source 154 (FIG. 3), which is controlled by the processor 156. Through the electrolysis process, water in the actuator liquid may result in hydrogen and oxygen molecules. In some embodiments, the electrodes 202, 204 may be interdigitated for efficient and effective electrolysis.

Some embodiments include a catalyst disposed within the gas generation chamber 200. The catalyst may promote recombination of gas molecules to reform the actuator liquid. In some embodiments, the catalyst is formed on inner surfaces of the gas generation chamber 200. The catalyst may be formed of rings or material extending about the chamber. In one embodiment, the catalyst includes platinum. Other embodiments use other catalyst materials.

In the example shown, the passageway 192 includes a first portion 194 extending adjacent a boss 196 that is arranged to cooperate with the flow control system 188 to control drainage fluid flow. The passageway 192 also includes a second, larger portion 198 configured in the embodiment shown as a chamber adjacent the boss 196, that less actively impacts the flow through the plate 106. In accordance with this, the first portion 194 of the fluid flow passageway 192 is formed to be substantially perpendicular to the general plane of the flexible membrane 190, and the upper surface of the boss 196 is arranged to be substantially parallel to the general plane of the flexible membrane 190. As such, flow through the first portion 194 is directed in the direction of and directly at the flexible membrane 190. Because of this, the drainage fluid is forced to redirect at an angle of about 90 degrees, although other angles are contemplated. Because of this arrangement, the flexible membrane 190 in this exemplary embodiment can more easily displace only slightly, but still provide a significant modification in the drainage flow. This occurs because the flexible membrane 190 may act in some respects as a cap on the first portion 194 of the fluid flow passageway. In some aspects, the flexible membrane 190 is arranged to cover the entire upper surface of the boss 196, and may even stretch to extend at least partially along the sides of the boss 196 adjacent the edge between the top of the boss 196 and the sides. Accordingly, in such embodiments, the flexible membrane 190 may largely limit or entirely cut off flow through the flow system 170.

Some alternative examples of the fluid flow passageway 192 include flexible membrane material that may displace to affect fluid flow through the passageway from more than one direction. In some examples, the flexible membrane 190 acts as a toroid or sphincter, with the passageway extending through the hollow center or orifice. In other examples the flexible membrane 190 is disposed on two sides of the passageway 192. In some of these examples, the sides are on opposing sides of the passageway 192. Some of these embodiments may have two or more separate flexible membranes that cooperate to limit the cross-sectional area of the fluid flow passageway 192. In one embodiment, the fluid flow is primarily in a direction parallel to the surface of the membrane from one side to the other.

Although FIG. 4 shows the flow system 170 as a valve, other embodiments of the flow system are pumps. Some of these embodiments differ from the embodiment in FIG. 4 by including a check valve at the entrance port 184 and exit port 186 that each permit one-way fluid flow. Alternating displacement of the membrane may draw drainage fluid into the pump through the entrance port 184 and push fluid out of the pump through the exit port 186.

Figure 5:
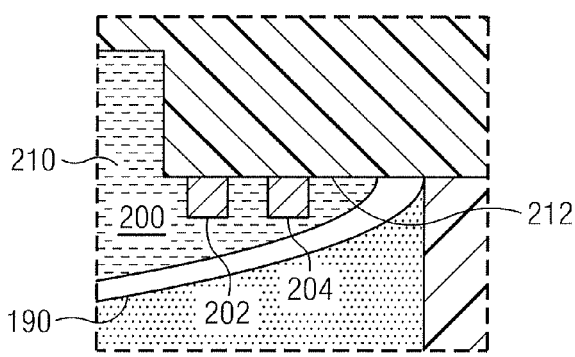
FIG. 5 is a stylized illustration of an enlarged portion of FIG. 4 according to the principles of the present disclosure.

FIG. 5 shows a close up of the cross-section placed at the apex of the membrane 190 inside the gas generation chamber 200. As can be seen, the membrane 190 extends from the housing and is arranged to span over the electrodes 202, 204 forming a gap 210 between the electrodes 202, 204 and the membrane 190. In this embodiment, since the electrodes 202, 204 are disposed adjacent the apex 212 of the membrane 190, the gap 210 is so small that it operates via capillary action to draw the actuator liquid into the gap 210, toward the apex 212, and onto the electrodes 202, 204. Capillary action operates by the surface tension of the liquid and adhesive forces between the liquid and the surrounding surfaces to draw or lift the liquid towards the electrodes 202, 204. Accordingly, the gap size and the location of the electrodes 202, 204 adjacent the membrane apex 212 are configured so that the electrodes that remain wetted via capillary action regardless of the orientation of the chamber.

Figure 6:
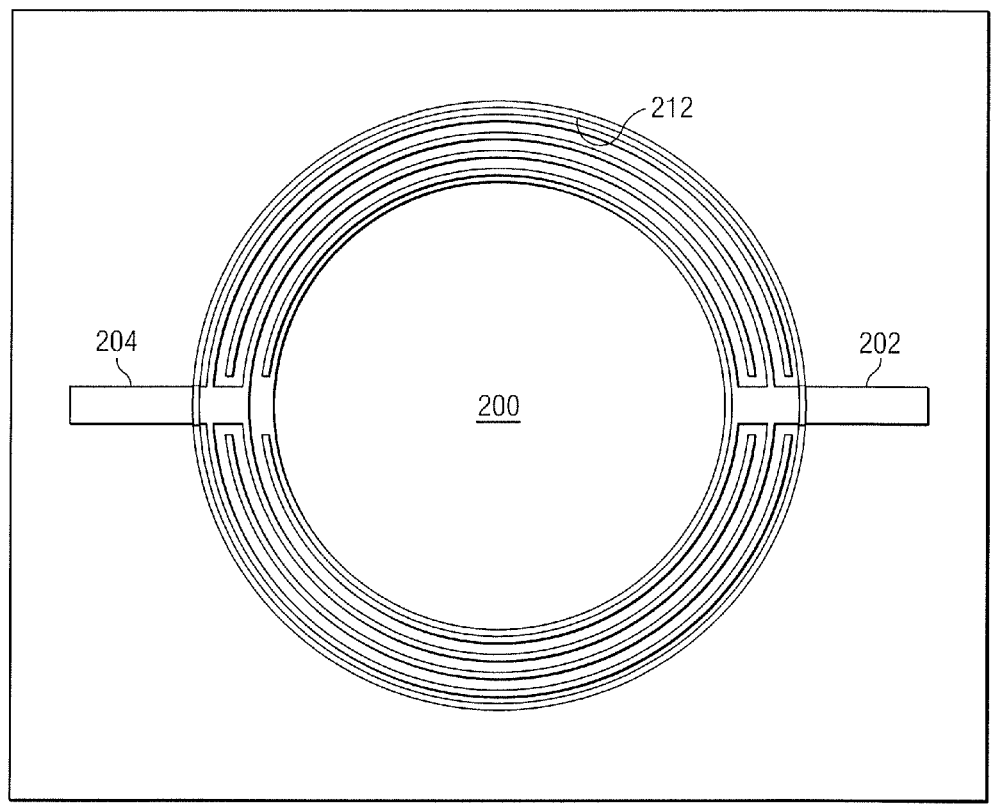
FIG. 6 is a stylized illustration of a portion of the exemplary flow system of FIG. 4 according to the principles of the present disclosure.
Figure 7:
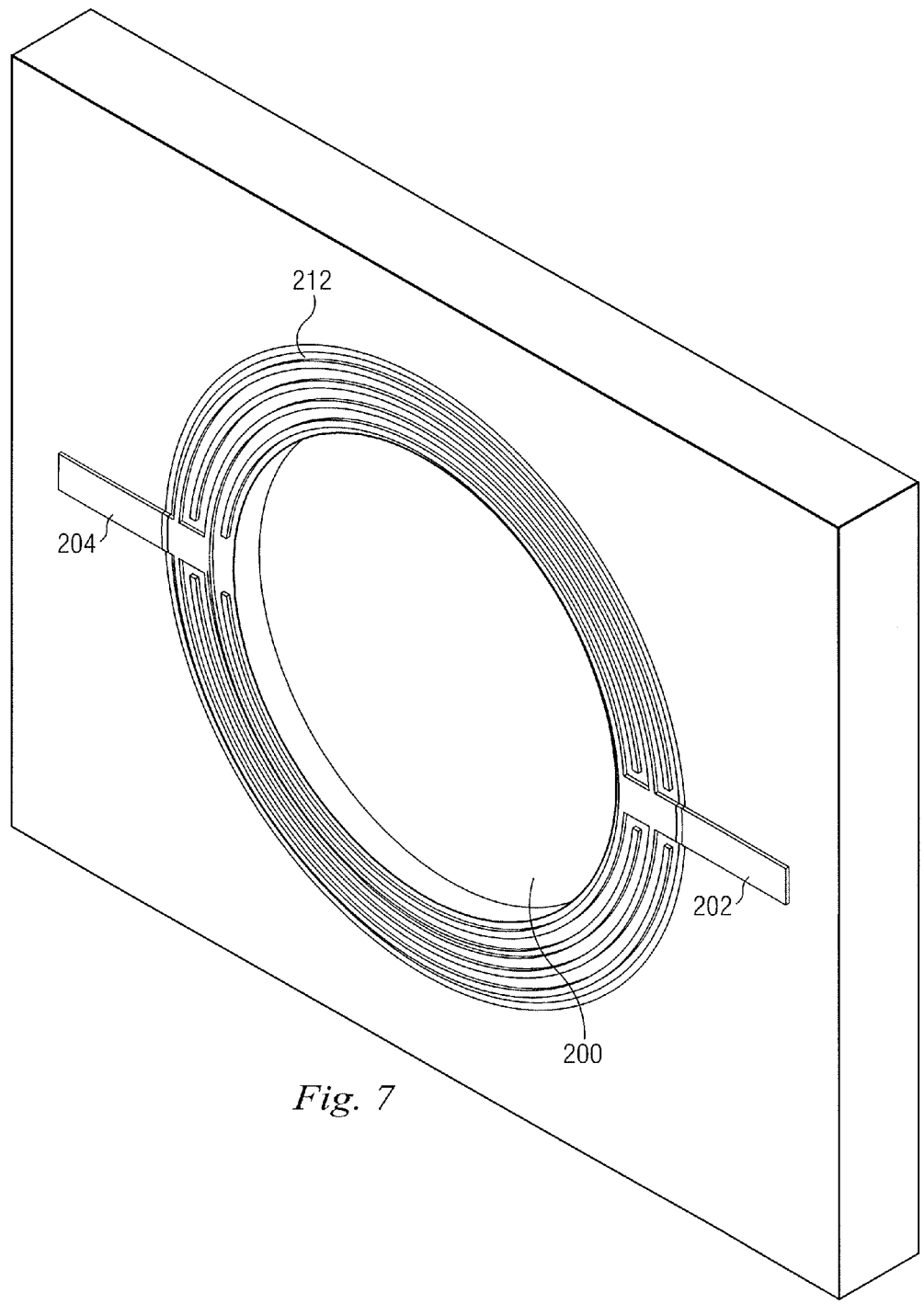
FIG. 7 is a stylized illustration of a portion of the exemplary flow system of FIG. 4 according to the principles of the present disclosure.

FIGS. 6 and 7 show additional views of the chamber portion 174 of the housing 172 with the membrane removed, facing the electrodes 202, 204. In this embodiment, in order for the electrodes 202, 204 to maintain a wetted condition via a capillary action, the electrodes 202, 204 are formed in a manner placing them adjacent the edge or apex of the membrane. Although the membrane is not shown in FIGS. 6 and 7 in order to show the electrodes, the location of the membrane and the location of the apex are still apparent in FIGS. 6 and 7. In the embodiment shown, the electrodes extend circumferentially along the location of the membrane apex 212. In this embodiment, each of the electrodes 202, 204 includes inter-digitating fingers that extend substantially along the entire length of the apex 212 of the membrane. In the example shown, the interdigitated electrodes include fingers extending circumferentially about the gas generation chamber 200. The arrangement and location ensures that gas generation occurs as the orientation of the flow system 170 changes. In addition, the circumferential nature of the electrodes ensures that even if the flow-regulating actuator 120 were oriented on its side as shown in FIG. 5, such that the upper portion of the electrodes may interface with gas, while the fluid is maintained in a lower region, at least a portion of the electrodes is always submerged and the gas generation and the corresponding fluid flow regulation may be maintained as desired.

While the example in FIGS. 5-7 shows a circular membrane and circular inter-digited electrodes, other embodiments are more rectangular shaped, oval shaped, or otherwise shaped. In embodiments having corners, such as rectangular shaped, the corners may be rounded. In each of these, the electrodes are disposed adjacent the apex of the membrane in a manner forming a gap and invoking capillary action. In some embodiments the electrodes may be circular and locate adjacent to each other but not inter-digited, or may be arranged such that the anode and cathodes are on opposite sides.

Figure 8:
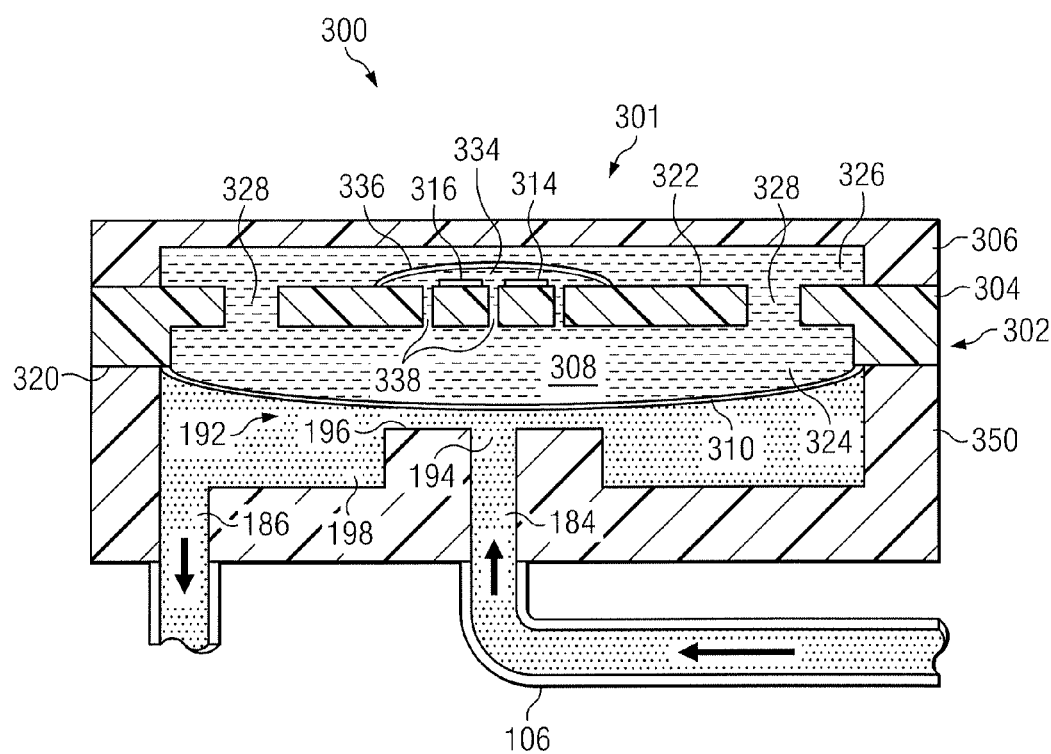
FIG. 8 is a stylized illustration of a cross-sectional view of an exemplary flow system that may be a part of an exemplary IOP control system according to the principles of the present disclosure.

FIG. 8 shows a stylized view of another embodiment of a flow system 300 that relies upon capillary action to maintain the electrodes in a wetted environment regardless of the orientation of the flow-regulating actuator 102. Since the flow passage portion of the flow system 300 may be similar to that described above, it will not be re-described, although similar reference numbers are used. However, the flow system includes a flow control system 301 that differs from the flow control system 188 described above.

The flow control system 301 in this embodiment is designed to maintain the electrode in a wet condition regardless of the orientation of the flow-regulating actuator 102. The flow control system 301 includes a housing 302 divided into a membrane housing portion 304 and an electrode housing portion 306. It also includes a flow control chamber 308, a membrane 310, and a plurality of electrodes 314, 316.

The membrane housing portion 304 and the electrode housing portion 306 may be each formed of glass or silicon wafers. In the example shown, these are stacked together, along with a flow passage portion 350 to provide a MEMS package formed of stacked wafers. Each of the housing portions may be formed with different structural features and then assembled or stacked together to form the overall flow system 300. It is worth noting that all the embodiments disclosed herein may be formed of stacked wafers. Some embodiments include Pt or Au electrical leads and electrodes for electrochemical actuation disposed on the membrane housing portion 304, at the interface of the membrane housing portion 304 and the electrode housing portion 306.

The membrane housing portion 304 includes a membrane facing surface 320 and an opposing electrode facing surface 322. The membrane facing surface 320 interfaces with and supports the membrane 310. The membrane 310 may be similar to that discussed above. The electrode facing surface 322 faces toward the electrode housing portion 306. This surface 322 interfaces with the electrodes and/or the electrode housing portion 306.

The flow control chamber 308 is divided into two main chambers, referred to as a membrane side chamber 324 and an electrode side chamber 326. The membrane side chamber 324 is formed as a recess within the membrane housing portion 304 and is defined in part by the membrane 310. The electrode side chamber 326 is formed by the electrode facing surface 322 and the electrode housing portion 306. These two chambers are in fluid communication through flow passages 328. These flow passages 328 are sized to permit substantially free flow of fluid from the one chamber to the other. In some embodiments, however, they may be shaped to inhibit free flow of gas bubbles in the liquid from passing freely between the chambers. This may be done, for example, by tapering the passage, lengthening the passage, or otherwise modifying the passage.

In this embodiment, the flow control system 301 includes a sub-chamber 334 formed within the flow control chamber 308. Here, the sub-chamber 334 is defined by a portion of the electrode facing surface 322 of the membrane housing portion 304 and defined by a second flexible membrane portion, referred to herein as a sub-membrane 336. The sub-chamber 334 contains the electrodes 314, 316 therein. Accordingly, the electrolysis process of phase-changing liquid to gas may occur within the sub-chamber 334 therefore defining it as a gas generation chamber.

The sub-membrane 306 may be formed of the same material and may be similar to the membrane 310 and membrane 190 discussed above. In some embodiments, the sub-membrane 310 may permit gas molecules to pass from inside the sub-chamber 334 to outside the sub-chamber and into the electrode side chamber 326. As liquid is phase-changed to gas via the electrolysis process, the gas molecules pass though the sub-membrane 336 and coalesce inside the electrode side chamber 326. As the liquid phase-changes to gas, the volume of the flow control chamber 308 changes, displacing the membrane 310 into the flow passageway 192 to regulate flow through the system 300.

Capillary passages 338 feed actuator liquid from the flow control chamber 308 to the electrodes 314, 316 in the sub-chamber 310. These capillary passages having opposing surfaces with a gap therebetween that is sized to promote capillary action of the actuator liquid. These surfaces may form opposing inner surfaces of a cylindrical tube or lumen or may have other shapes. As liquid at the electrodes is phase-changed to gas, additional liquid is continuously drawn to the electrodes via capillary action through the capillary passages 338. Accordingly, the capillary passages 338 are sized and formed to permit liquid flow through the passages to the electrodes using the surface tension of the liquid. Accordingly, regardless of the orientation of the flow-regulating actuator 102, the capillary passages 338 may feed liquid to the electrodes 314, 316.

In some embodiments, methods of directing flow of fluid through the system include obtaining pressure data with sensors disposed about a patient's eye and/or about the flow-regulating actuator 102. Based on the sensed data, the processor 156 may obtain IOP or otherwise obtain a value representative of IOP. If the IOP is higher or lower than desired, the control system 150 may adjust flow through the implantable actuator using the flow control systems described herein.

For example, aqueous humor from the anterior chamber of the patient's eye, as a drainage liquid, may flow through the passageway 192 of the flow system. Regulation of the drainage liquid flow occurs by converting the actuation fluid to gas in the gas generation chamber. The conversion may occur via an electrolysis process using a cathode electrode and an anode electrode. As the electrolysis process occurs, the actuation liquid immediately adjacent the electrodes may convert to gas. In order to provide additional drainage flow regulation, additional actuator liquid may be drawn to interface with the electrodes. In addition, since the flow-regulating actuator 102 may be disposed in any orientation at any given time, it is possible that gravity may act on the actuator liquid and a portion of the electrodes will be disposed within the gaseous region and unable to carry out the electrolysis process on the actuator liquid. In the embodiments shown, capillary action operates to maintain actuator liquid in communication with the electrodes. Accordingly, actuator liquid may be drawn to the electrodes as the surface tension of the actuator liquid acts on the surface of the electrode and a surface of an adjacent surface, such as the membrane. In addition, the electrodes are disposed about substantially entirely around the perimeter of the membrane. In this example, it is at the apex. As used herein, substantially entirely about the perimeter of the membrane means greater than about 75% of the way around the perimeter, although the electrodes may extend around a greater length or a smaller length of the perimeter. Alternatively, the liquid may be drawn into contact with the electrodes by locating the electrodes adjacent openings to capillary passages disposed in the flow control system.

As the liquid converts to gas, the volume within the gas generation chamber increases. As the volume increases, the remaining fluid applies increased pressure against the membrane, which may distend into the flow passageway, changing the size of the passageway in a manner that modifies the flow rate of the drainage fluid.

It is worth noting that reversing the polarities of the electrodes will result in the gas bubbles phase changing into liquid. Accordingly, in some aspects, the system may speed the conversion of the gas molecules back to liquid, to decrease the pressure and therefore the volume of the gas generation chamber.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A fluid flow-regulating system, comprising:
   an electrolysis chamber configured to contain a liquid;
   first and second electrodes disposed within the electrolysis chamber;
   a flexible membrane partially defining the electrolysis chamber to contain the liquid; and
   a gap between opposing surfaces within the electrolysis chamber, the gap sized to promote capillary action of a liquid in the electrolysis chamber that draws the liquid to at least one of the first and second electrodes in a manner allowing the flow-regulating system to be placed in multiple orientations and still have said one of the first and second electrodes wetted by capillary action as the flexible membrane contracts or expands in response to an electrolysis process performed in the electrolysis chamber.

2. The fluid flow-regulating system of claim 1, wherein one of said opposing surfaces is a surface of one of the first and second electrodes and another of said opposing surfaces is a surface of the flexible membrane.

3. The fluid flow-regulating system of claim 2, wherein the first and second electrodes extend adjacent an apex of the flexible membrane.

4. The fluid flow-regulating system of claim 1, wherein the first and second electrodes extend substantially about the complete perimeter of the electrolysis chamber.

5. The fluid flow-regulating system of claim 1, wherein said opposing surfaces are surfaces of a capillary channel having an opening adjacent one of the first and second electrodes.

6. The fluid flow-regulating system of claim 4, comprising a sub-chamber within the electrolysis chamber, the first and second electrodes being disposed within the sub-chamber and the opening of the passageway opening into the sub-chamber.

7. The fluid flow-regulating system of claim 1, comprising:
   a fluid flow passageway; and
   a displaceable structure between the fluid flow passageway and the electrolysis chamber, wherein the displaceable structure is configured to affect fluid flow through the fluid flow passageway as a result of pressure changes within the electrolysis chamber.

8. The fluid flow-regulating system of claim 7, wherein the displaceable structure is an additional flexible membrane.

9. A fluid flow-regulating system for an ocular implant sized for implantation in an eye of a patient for treating an ocular condition, comprising:
   a housing including an entrance port and an exit port connected by a fluid flow passageway;

a gas generation chamber within the housing;

a gas generating element associated with the gas generation chamber, the gas generating element being operable to convert liquid to gas;

a gap between opposing surfaces, the gap sized to promote capillary action of a liquid in the gas generation chamber that draws the liquid to the gas generating element in a manner allowing the housing to be placed in multiple orientations and still have the gas generating element wetted by capillary action; and a displaceable member between the fluid flow passageway and the gas generation chamber, the displaceable member being moveable relative to the fluid flow passageway to affect fluid flow through the passageway.

10. The fluid flow-regulating system of claim 9, wherein the gas generating element comprises an anode electrode and a cathode electrode and is operable to convert liquid to gas via an electrolysis process.

11. The fluid flow-regulating system of claim 10, wherein one of said opposing surfaces is a surface of the gas generating element and another of said opposing surfaces is the displaceable member.

12. The fluid flow-regulating system of claim 9, wherein the gas generating element is a pair of electrodes extending along a periphery of the gas generation chamber.

13. The fluid flow-regulating system of claim 9, wherein the gas generating element comprises a first electrode and a second electrode disposed along a perimeter of the gas generation chamber, the first and second electrodes being interdigitated.

14. The fluid flow-regulating system of claim 9, wherein said opposing surfaces are surfaces of a capillary channel having an opening adjacent the gas generating element.

15. The fluid flow-regulating system of claim 14, comprising a catalyst disposed in the gas generation chamber, the catalyst being configured to promote recombination of molecules to a liquid state.

16. The fluid flow-regulating system of claim 9, comprising a sub-chamber within the gas generation chamber, the sub-chamber containing the gas generating element.

17. The fluid flow-regulating system of claim 16, wherein the sub-chamber is disposed centrally within the gas generation chamber.

* * * * *